(12) United States Patent
Palomo (10) Patent No.: US 9,717,576 B1
(45) Date of Patent: Aug. 1, 2017

(54) DENTAL IMPLANT CLEANING AND CHEMOTHERAPEUTIC TREATMENT DEVICES, KITS, AND METHODS

(71) Applicant: Leena Palomo, Pepper Pike, OH (US)

(72) Inventor: Leena Palomo, Pepper Pike, OH (US)

( * ) Notice: Subject to any disclaimer, the term of this patent is extended or adjusted under 35 U.S.C. 154(b) by 0 days.

(21) Appl. No.: 15/335,767

(22) Filed: Oct. 27, 2016

(51) Int. Cl.
| | |
|---|---|
| *A61C 3/00* | (2006.01) |
| *A61C 17/22* | (2006.01) |
| *A46B 9/02* | (2006.01) |
| *A46D 1/00* | (2006.01) |
| *A46B 3/18* | (2006.01) |
| *A46B 9/04* | (2006.01) |

(52) U.S. Cl.
CPC .............. *A61C 17/222* (2013.01); *A46B 3/18* (2013.01); *A46B 9/025* (2013.01); *A46B 9/04* (2013.01); *A46D 1/0207* (2013.01)

(58) Field of Classification Search
CPC ......... A61C 17/222; A46B 3/18; A46B 9/025; A46B 9/04; A46D 1/0207
See application file for complete search history.

(56) References Cited

U.S. PATENT DOCUMENTS

| | | | | |
|---|---|---|---|---|
| 5,681,335 | A * | 10/1997 | Serra | A61B 17/3207 606/159 |
| 6,715,603 | B1 * | 4/2004 | Uribe | A61C 15/00 206/232 |
| 2003/0224320 | A1 * | 12/2003 | Kandelman | A46B 7/04 433/80 |
| 2009/0222023 | A1 * | 9/2009 | Boone, III | A61B 17/545 606/131 |
| 2011/0033817 | A1 * | 2/2011 | McKay | A46D 1/00 433/29 |
| 2012/0129129 | A1 | 5/2012 | Fehr et al. | |
| 2014/0000049 | A1 | 1/2014 | Lyngstadaas | |
| 2015/0238294 | A1 | 8/2015 | Coopersmith | |

* cited by examiner

*Primary Examiner* — Heidi M Eide
(74) *Attorney, Agent, or Firm* — Renner, Otto, Boisselle & Sklar, LLP (57) ABSTRACT

A dental implant cleaning or chemotherapeutic treatment device includes an elongated hollow stem, and bristles operably attached to the elongated hollow stem adjacent a first end of the elongated hollow stem and projecting from the elongated hollow stem nonparallel to the elongated hollow stem.

6 Claims, 7 Drawing Sheets

DENTAL IMPLANT CLEANING AND CHEMOTHERAPEUTIC TREATMENT DEVICES, KITS, AND METHODS

FIELD OF THE INVENTION

The present disclosure relates generally to cleaning and chemotherapeutic treatment of dental implants.

BACKGROUND

Conventional cleaning and chemotherapeutic treatment of dental implants often produces unsatisfactory results. In dealing with long standing dental implants in patients, there is no reliable way to maintain a dental implant once it becomes symptomatic. Peri-implant mucositis and peri-implantitis, for example, are significant problems. Using conventional devices and methods, dentists often wrestle with these issues until the implant fails or abscesses. Then the implant is often trephined out causing trauma to adjacent tissue and requiring more complex reconstruction involving significantly more morbidity. Instrumenting the defect in order to achieve degranulation, debridement, and disinfection, which is meant for removal of tissue tags, biofilm, debris, calculus, residual cements etc., all harboring pathogens, has been a challenge.

Implant surface properties vary widely among all the permutations and combinations of implant coatings (e.g., carbon, bisphosphonates, bone stimulating factors, bioactive glass and bioactive ceramics, fluoride, hydroxyapatite, calcium phosphate, and titanium/titanium nitride) and their applications mechanisms (e.g., plasma spraying, hydro-coating, and nanoscale technology). To avoid damaging the implant surface and sparking, dentists often avoid using metal instruments against a metal implant. Plastic or polymer scaling instruments are marketed for this purpose, but fall short in their effectiveness against the sometimes tenacious material which must be removed from the site. Also, conventional instruments are often too large to fit the peri-implant defect. Use of air powder abrasive and laser treatment as implant surface cleaning methods is not wide enough to draw definitive conclusions. Some dentists use stainless steel or metal alloy bur devices, but such metal to metal contact leaves not only the coating, but also screws on the implant surface, vulnerable to different degrees of damage.

The state of the art in peri-implant debridement appears to be mechanical debridement using a plastic manual hand scaler. But the short comings of such plastic scalers have been documented. Other mechanical debridement methods include the use of titanium bristles devices in combination with a high speed dental hand piece (see, e.g., U.S. Pat. App. Pub. No. 2012/0129129 to Fehr) which has been suggested as being "kinder" to the implant surface. These devices, however, have not gained popularity for several potential reasons. First, the wear characteristics of titanium and its alloys of the devices against titanium implants are well known to create exponentially accelerated wear of the devices. This results in attrition and diffusion and subsequent failure of the titanium bristle, which can result in particles being lost into the defect or, more generally, into the oral cavity. Additionally, the heat generated by the metal to metal contact cannot easily be contained considering that a very small temperature increment in a biologic environment can lead to bone necrosis and damage to pulpal tissue of adjacent teeth. Keeping in mind that such defects intended for instrumentation are generally just a few cubic millimeters in volume, there appears to be no instrument which is soft enough to not injure the biologic surfaces and still effectively achieve debridement.

To address these issues, implant manufactures have suggested mechanical debridement coupled with chemotherapeutics treatment aiming to disinfect and condition the area. However considering the viscosity of chemotherapeutics such as, but not limited to antibiotics, antiseptics, disodium salts, etc. against surface porosity and tortuous screw or bone like configurations (having surfaces which counter gravity), no instrument is both strong enough to bear and hold the agent and delicate enough to deliver the chemotherapeutic into implant configurations particularly in deeper defects. The Fehr instrument, for example, is designed to deliver EDTA to the site for the purpose of tissue conditioning. But, its titanium bristles may not be optimal for delivering various viscosity chemotherapeutics into a tortuous space.

SUMMARY OF THE INVENTION

The present disclosure provides methods, devices and kits to address these problems. The present disclosure describes a series of brush devices designed for treating (including but not limited to degranulating, debriding, disinfecting, and applying chemotherapeutics) to peri-implant lesions and defects. Each brush device may be made of a metallic core "trunk" with tufts of bristles which extend out to various distances in various patterns. The central core may have a latch lock on the non-working end, which may insert into a motorized dental implant handpiece such that the brush devices may operate as rotary devices at various speeds and torques adjusted through the implant hand piece motor. Alternatively, the brush devices may also be manually activated.

The first brush in the series may have a nylon-bristled central metal core designed to debride, degranulate and remove biologic biofilm and adherent debris, etc. An operator may select any number of tuft configurations for this step. Alternatively, the operator may select a sequence of tuft configurations to clean the peri-implant defect. The brush devices may be used manually or on the implant hand piece attached to a motor at a range of RPMs and torques required to remove tissue tags, debris, biofilm, necrotic material, cement or any number of material which harbors pathogenic material.

Since a range of torques and RPMs are used to remove the sometimes tenacious material in this step, the invention provides means for retrieval in case a portion of the brush device separates into the defect. The central metal core may have a retrieval thread attached to one end. If a portion of the device separates, the cord or thread extends outside of the oral environment and pulling on it can retrieve the separated portion of the device. The brush device may also be attached to an accompanying fiber optic camera for the purpose of visualizing defects. Also, because the central core is hollow, it allows for lavage and/or cooling fluid to be transported from the non-working end to the working end of the device.

The second brush in the series may have a calf hair-bristled central metal core. This step and calf hair brush device may be used to "pick up" and apply chemotherapeutic to the peri-implant environment, reaching into the implant surface pores. Different chemotherapeutics may have differing action mechanisms. These range from antiseptic to antibiotic to tissue conditioning to anticollagenolytic actions. With such a range of chemotherapeutics, there is a need for a bristle fine enough to apply varying viscosity materials to the porous and tortuous implant surface, but also strong enough to carry the material on its surface for delivery. Through experimentation, the inventor finds that calf hair bristles work very well for this purpose.

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Unlike the device of Fehr which has a broader focus on natural teeth and implants, the brush devices, kits, and methods of the present disclosure are specifically focused on implant lesions. Inflammatory activity around implants is greater than around natural teeth and the tissues are more susceptible to the spread of plaque-associated infections into alveolar bone. When cases of peri-implantitis were systematically compared to cases of periodontitis, the results revealed tissue destruction to be more severe in peri-implantitis. One explanation for the increased rate of progression and greater severity of tissue destruction is the structural differences between periodontal and peri-implant tissues. Unlike natural teeth, dental implants do not have cementum or Sharpey's fibers, they are not bounded by periodontal ligament, and, consequently, there is direct contact between bone and implant surface. It is axiomatic that infection can progress without impediments from soft to hard tissue. Peri-implant disease is an infection-induced inflammatory process associated with dental implants. Since the condition can affect both soft and hard tissues, it can be classified into two categories: peri-implant mucositis and peri-implantitis.

Peri-implant mucositis is soft tissue inflammation surrounding dental implants without evidence of bone loss. Frank peri-implantitis reflects progression of peri-implant mucositis and has both soft- and hard-tissue components. Although the term mucositis is used to describe soft tissue inflammation, there is disagreement in the literature whether histologically the soft tissue around a dental implant more closely resembles mucosa or gingiva. Nevertheless, the obvious pathogenic comparison of peri-implant mucositis is to gingivitis, where only the surrounding soft tissue shows inflammation and the alveolar crestal bone is intact. Predictably, like gingivitis, peri-implant mucositis is reversible. Peri-implantitis mirrors the pathogenesis of periodontitis.

Exposed titanium surfaces such as those of a dental implant accumulate glycoproteins forming a salivary pellicle and as bacteria move onto a surface, the dynamic process of biofilm formation begins. Implant-associated biofilm resembles that of chronic periodontitis, i.e., mixed, non-specific microbes, dominated by gram-negative anaerobes. A notable difference is the association of S. aureus with peri-implantitis. Therapy successfully reverses the inflammation which is characteristic to mucositis. Furthermore, peri-implantitis patients investigated, frequently yield bacteria resistant to clindamycin, amoxicillin, doxycycline, or metronidazole. Due to the wide variation in observed drug resistance patterns, antibiotic susceptibility testing of cultivable submucosal bacterial pathogens may aid in the selection a combination of antimicrobial therapy for peri-implantitis patients.

Adjunctive antibiotic therapy in addition to mechanical removal of plaque bacterial biofilms has been suggested. The present disclosure provides brush devices, kits, and methods specifically focused on cleaning and chemotherapeutic treatment of implant lesions. A non-calf hair bristles brush device is generally provided for mechanical cleaning and a calf hair bristles brush device is generally provided for chemotherapeutic treatment.

Figure 1:
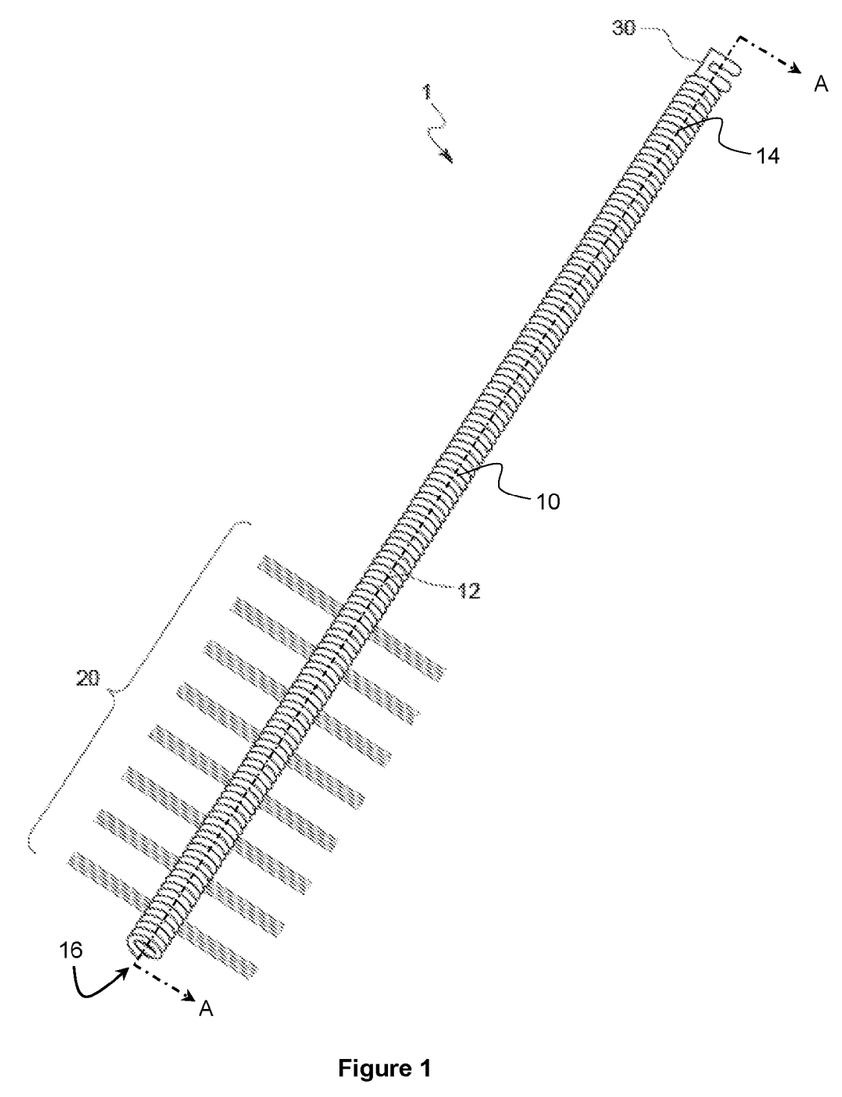
FIG. 1 illustrates a perspective view of an exemplary dental implant cleaning or chemotherapeutic treatment device.

FIG. 1 illustrates a perspective view of an exemplary dental implant cleaning or chemotherapeutic treatment device 1. The device 1 includes an elongated hollow stem 10 and bristles 20 operably attached to the elongated hollow stem 10 at a working end 12. The bristles 20 project from the elongated hollow stem 10 nonparallel (e.g., perpendicular) to the elongated hollow stem 10. The device 1 may also include a latch 30 operably attached at a non-working end 14 of the elongated hollow stem 10. The latch 30 may be used to connect the device 1 to a motorized rotational device to rotate the device 1 about the longitudinal axis/of the elongated hollow stem 10.

FIGS. 2A-2D illustrate cross-sectional views of the exemplary dental implant cleaning or chemotherapeutic treatment device 1 along the line A of FIG. 1. The elongated hollow stem 10 has a hollow cavity 16 along the length of the stem 10. Because of this hollow cavity 16, the elongated hollow stem 10 may be configured to transport fluid for lavage or cooling during dental implant cleaning or chemotherapeutic treatment from the non-working end 14 to the working end 12.

Figure 2A:
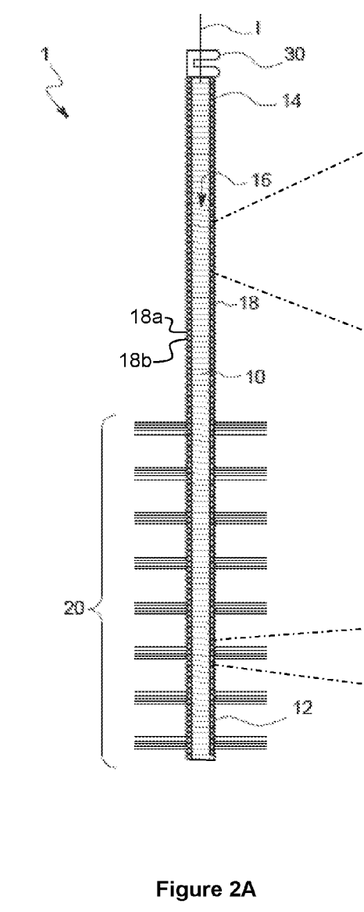
FIGS. 2A-2D illustrate cross-sectional views of the exemplary dental implant cleaning or chemotherapeutic treatment device along the line A of FIG. 1.
Figure 2B:
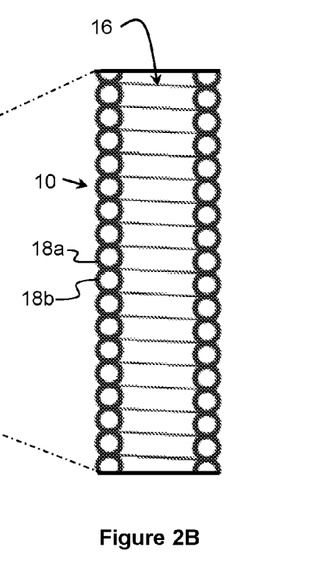
Figure 2C:
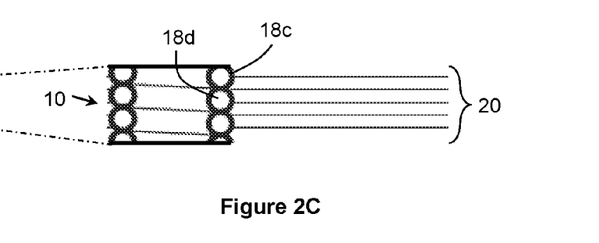
Figure 2D:
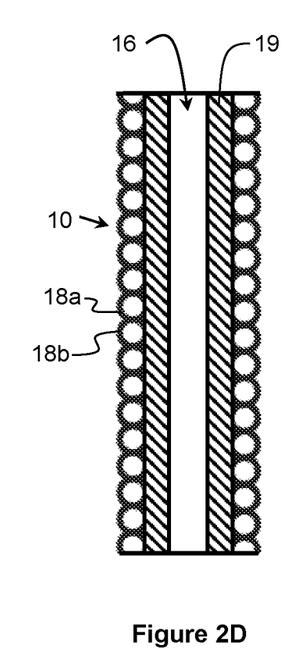

In the illustrated embodiment of FIGS. 2A-2C, the elongated hollow stem 10 is formed from a core 18 bent helically to form the elongated hollow stem 10. In this embodiment, the core 18 is bent helically with adjacent portions (e.g., 18a, 18b) of the core 18 touching such that the elongated hollow stem 10 may be configured to transport fluid for lavage or cooling from the non-working end 14 to the working end 12. In the embodiment of FIG. 2D, the core 18 is wrapped around a central tube 19. In this embodiment, the central tube 19 may be configured to transport fluid for lavage or cooling during dental implant chemotherapeutic treatment from the non-working end 14 to the working end 12.

The bristles 20 may be made of nylon or similar materials and, in a particularly novel embodiment, the bristles 20 may be made of calf hair. Calf hair in this context includes hair coming from guard hair forming an outer coat of a calf. As discussed above, nylon works well for cleaning a dental implant and its surroundings in vivo. On the other hand, through experimentation, the inventor finds that calf hair bristles work very well and superior to any conventional dental implant treating devices for the purpose of chemotherapeutic treatment. The brush device 1 with calf hair bristles 20 may be used, for example, to "pick up" and apply chemotherapeutic to the peri-implant environment, reaching into the implant surface pores.

As best shown in FIG. 2C, the bristles 20 may be operably attached to the elongated hollow stem 10 by being clasped between adjacent portions (e.g., 18*c*, 18*d*) of the helically bent core 18.

Figure 3:
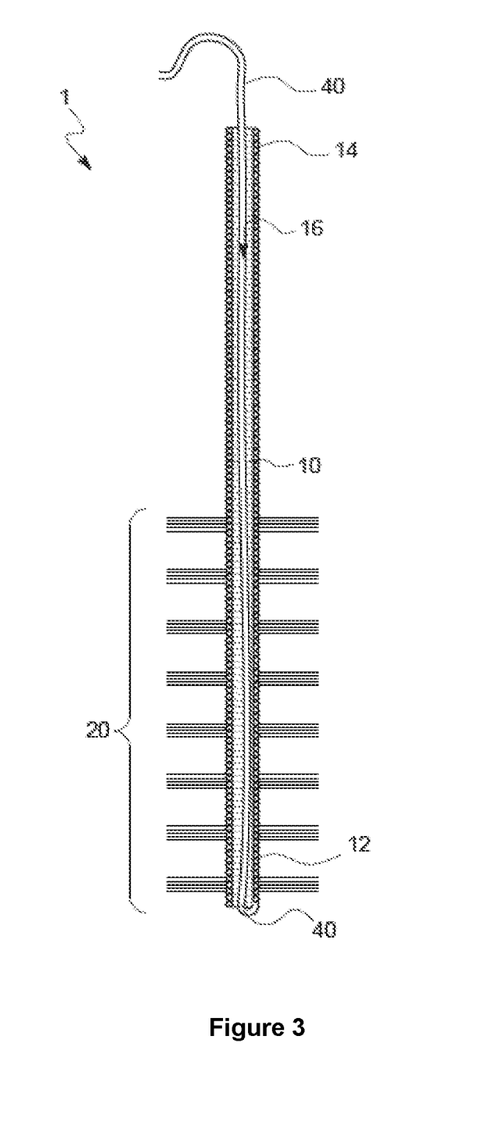
FIG. 3 illustrates a cross-sectional view of the exemplary dental implant cleaning or chemotherapeutic treatment device of FIG. 1 including a retriever cord.

FIG. 3 illustrates a cross-sectional view of the exemplary dental implant cleaning or chemotherapeutic treatment device 1 including a retriever cord 40. Because of the hollow cavity 16, the elongated hollow stem 10 may also be configured to transport the retriever cord 40. The retriever cord 40 is operably connected to the elongated hollow stem 10 towards the end of the working end 12. The retriever cord 40 is threaded through the hollow cavity 16 of the elongated hollow stem 10 and it may exit the elongated hollow stem at or near the non-working end 14. The cord 40 may be a nylon cord of about one yard length. Since the device 1 may be attached to a motorized device and a range of torques and RPMs may be used to remove the sometimes tenacious material adhered to the dental implant, there is a possibility that portions of the device 1 and particularly the elongated hollow stem 10 may separate. In such a case of separation of a portion of the device 1, the retriever cord 40 may be used to retrieve the separated portion from the oral cavity.

Because of the hollow cavity 16, the elongated hollow stem 10 may also be used with a fiber optic camera that may reside or at least some of its wiring may reside or travel in the hollow cavity 16 for the purpose of visualizing defects.

Figure 4:
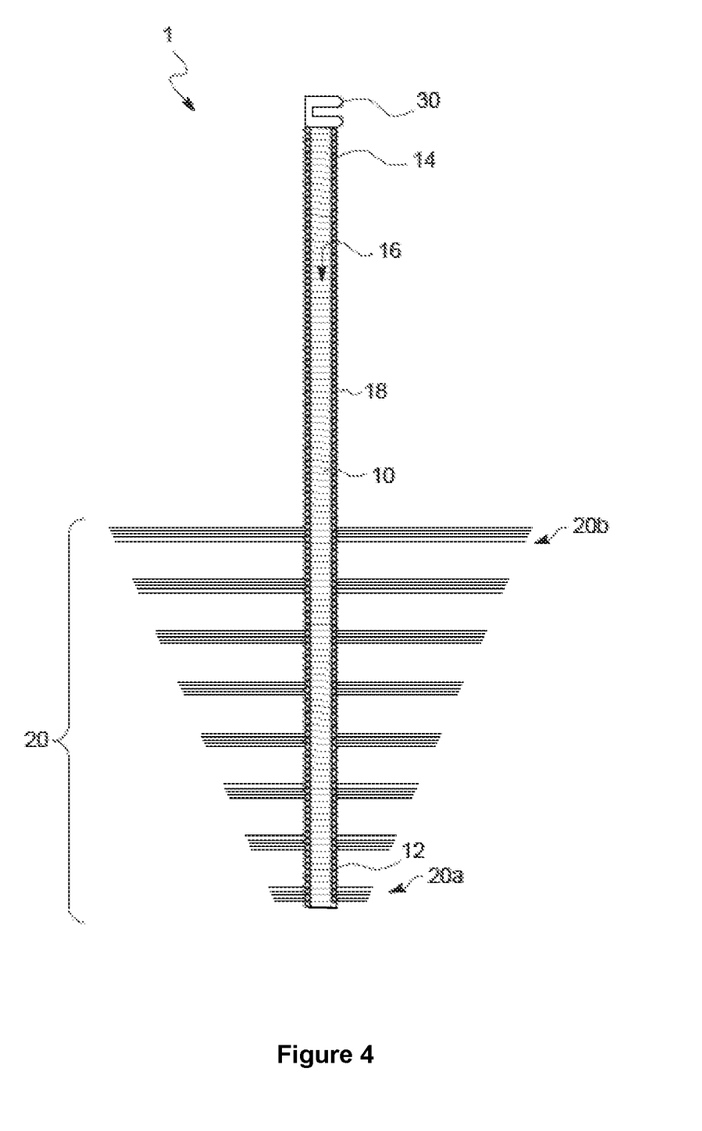
FIG. 4 illustrates a cross-sectional view of an exemplary dental implant cleaning or chemotherapeutic treatment device with a tapered bristle pattern or arrangement.
Figure 5:
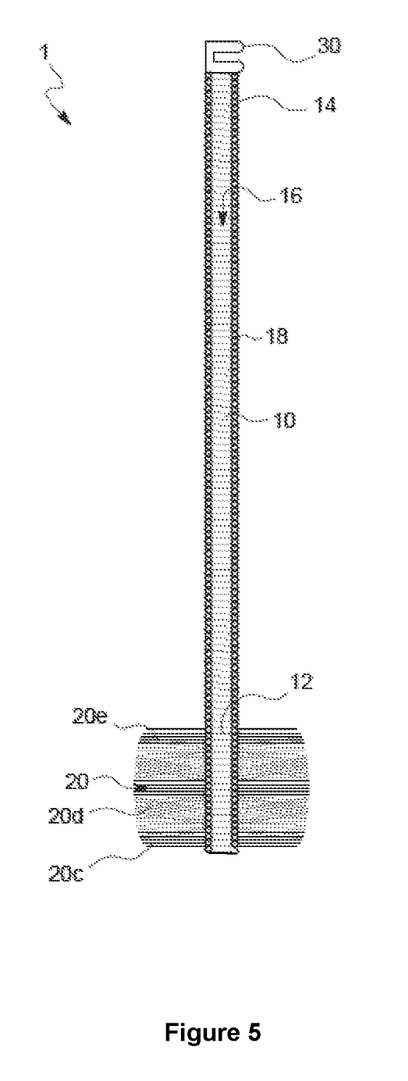
FIG. 5 illustrates a cross-sectional view of an exemplary dental implant cleaning or chemotherapeutic treatment device with a "tufted" bristle pattern or arrangement.

FIGS. 4 and 5 illustrate views of the exemplary dental implant cleaning or chemotherapeutic treatment device 1 with bristle patterns or arrangements different from the pattern or arrangement of FIGS. 1-3. FIGS. 1-3 illustrate the exemplary dental implant cleaning or chemotherapeutic treatment device 1 with a bristle pattern or arrangement in which the bristles 20 are of constant length or approximately constant length.

FIG. 4 illustrates the exemplary dental implant cleaning or chemotherapeutic treatment device 1 with a tapered bristle pattern or arrangement in which length of the bristles 20 increases from the bristles 20*a* near the very end of the working end 12 to the bristles 20*b* away from the very end of the working end 12 and towards the non-working end 14.

FIG. 5 illustrates the exemplary dental implant cleaning or chemotherapeutic treatment device 1 with a "tufted" bristle pattern or arrangement in which length of the bristles 20 increases in a curve from the bristles 20*c* near the very end of the working end 12 to the bristles 20*d* away from the very end of the working end 12 and decreases from the bristles 20*d* to the bristles 20*e* further away from the very end of the working end 12 towards the non-working end 14.

A dental implant chemotherapeutic treatment and cleaning kit, therefore, may include a series of brush devices 1, some designed for cleaning (e.g., degranulating, debriding, etc.) and others designed for applying chemotherapeutics.

A first cleaning brush device 1 may include bristles 20 made of a material other than calf hair such as nylon that works well for cleaning. Such a cleaning device would include the elongated hollow stem 10, which, since it includes the hollow cavity 16, may be configured to transport fluid for lavage or cooling during cleaning. Because of the hollow cavity 16, the elongated hollow stem 10 may also be configured to transport a retriever cord or a fiber optic camera that may reside or at least some of its wiring may reside or travel in the hollow cavity 16 for the purpose of visualizing defects.

A second chemotherapeutic treatment device 1 may include calf hair bristles 20 that work well for chemotherapeutic treatment. Such a chemotherapeutic treatment device would include the elongated hollow stem 10, which, since it includes the hollow cavity 16, may be configured to transport fluid for lavage or cooling during chemotherapeutic treatment. Because of the hollow cavity 16, the elongated hollow stem 10 may also be configured to transport a retriever cord or a fiber optic camera that may reside or at least some of its wiring may reside or travel in the hollow cavity 16 for the purpose of visualizing defects.

Either device in the kit, may include a latch 30 operably connected adjacent the non-working end 14 of the elongated hollow stem 10 for connecting to a motorized rotational device to rotate the cleaning device or the chemotherapeutic treatment device about a longitudinal axis of the first elongated hollow stem.

Figure 6:
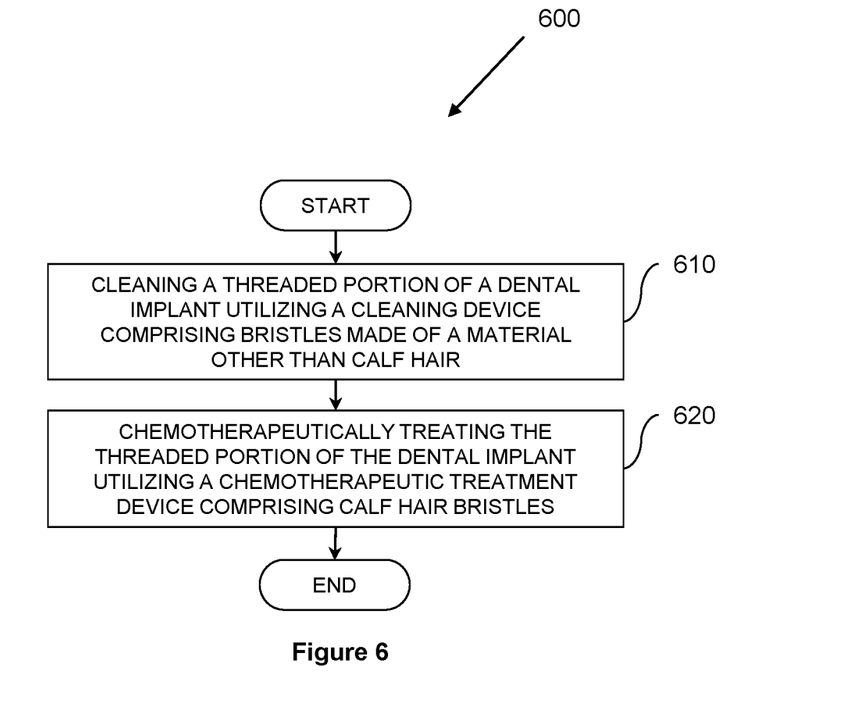
FIG. 6 illustrates a flow diagram for an exemplary method for dental implant chemotherapeutic treatment and cleaning.

Exemplary methods may be better appreciated with reference to the flow diagram of FIG. 6. While for purposes of simplicity of explanation, the illustrated methodologies are shown and described as a series of blocks, it is to be appreciated that the methodologies are not limited by the order of the blocks, as some blocks can occur in different orders or concurrently with other blocks from that shown and described. Moreover, less than all the illustrated blocks may be required to implement an exemplary methodology. Furthermore, additional methodologies, alternative methodologies, or both can employ additional blocks, not illustrated.

FIG. 6 illustrates a flow diagram for an exemplary method 600 for dental implant chemotherapeutic treatment and cleaning. At 610, the method 600 includes cleaning a threaded portion of a dental implant utilizing a cleaning device comprising bristles made of a material other than calf hair (e.g., nylon). At 620, the method 600 also includes chemotherapeutically treating the threaded portion of the dental implant utilizing a chemotherapeutic treatment device comprising calf hair bristles.

While the figures illustrate various actions occurring in serial, it is to be appreciated that various actions illustrated could occur substantially in parallel, and while actions may be shown occurring in parallel, it is to be appreciated that these actions could occur substantially in series. While a number of processes are described in relation to the illustrated methods, it is to be appreciated that a greater or lesser number of processes could be employed and that lightweight processes, regular processes, threads, and other approaches could be employed. It is to be appreciated that other exemplary methods may, in some cases, also include actions that occur substantially in parallel. The illustrated exemplary methods and other embodiments may operate in real-time, faster than real-time in a software or hardware or hybrid software/hardware implementation, or slower than real time in a software or hardware or hybrid software/hardware implementation.

DEFINITIONS

The following includes definitions of selected terms employed herein. The definitions include various examples or forms of components that fall within the scope of a term and that may be used for implementation. The examples are not intended to be limiting. Both singular and plural forms of terms may be within the definitions.

An "operable connection," or a connection by which entities are "operably connected" or "operatively connected" is one in which the entities are connected in such a way that the entities may perform as intended. An operable connection may be a direct connection or an indirect connection in which an intermediate entity or entities cooperate or otherwise are part of the connection or are in between the operably connected entities.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and so on, have been illustrated by describing examples, and while the examples have been described in considerable detail, it is not the intention of the applicants to restrict or in any way limit scope to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

What is claimed is:

1. A dental implant chemotherapeutic treatment and cleaning kit comprising:
    a cleaning device comprising:
        a first elongated hollow stem having a first end and a second end opposite the first end; and
        bristles made of a material other than calf hair and operably attached to the first elongated hollow stem at the second end of the first elongated hollow stem; and
    a chemotherapeutic treatment device comprising:
        a second elongated hollow stem having a first end and a second end opposite the first end; and
        calf hair bristles operably attached to the second elongated hollow stem at the second end of the second elongated hollow stem; and
    a retriever cord operably connected to the first elongated hollow stem or the second elongated hollow stem at the second end of the first elongated hollow stem or the second end of the second elongated hollow stem, threaded through a hollow interior of the first elongated hollow stem or the second elongated hollow stem, and exiting the first elongated hollow stem or the second elongated hollow stem at or near the first end.

2. The dental implant cleaning or chemotherapeutic treatment device kit of claim 1, wherein the first elongated hollow stem or the second elongated hollow stem includes a core bent helically to form the first elongated hollow stem or the second elongated hollow stem.

3. The dental implant cleaning or chemotherapeutic treatment device kit of claim 1, wherein the first elongated hollow stem or the second elongated hollow stem includes a core bent helically to form the first elongated hollow stem or the second elongated hollow stem with adjacent portions of the core touching such that wherein the first elongated hollow stem or the second elongated hollow stem is configured to transport fluid for lavage or cooling to the first end.

4. The dental implant cleaning or chemotherapeutic treatment device kit of claim 1, wherein the first elongated hollow stem or the second elongated hollow stem includes a core bent helically to form the first elongated hollow stem or the second elongated hollow stem, and the core is wrapped around a central tube.

5. The dental implant cleaning or chemotherapeutic treatment device kit of claim 1, wherein the first elongated hollow stem or the second elongated hollow stem includes a core bent helically to form the first elongated hollow stem or the second elongated hollow stem and the bristles or the calf hair bristles are operably attached to the first elongated hollow stem or the second elongated hollow stem by being clasped between adjacent portions of the helically bent core.

6. The dental implant cleaning or chemotherapeutic treatment device kit of claim 1, comprising:
    a latch operably connected adjacent the first end of the first elongated hollow stem or the first end of the second elongated hollow stem, the latch configured to connect to a motorized rotational device to rotate the cleaning device or the chemotherapeutic treatment device about a longitudinal axis of the first elongated hollow stem or the second elongated hollow stem.

* * * * *